United States Patent
Dolan

(10) Patent No.: US 7,377,937 B2
(45) Date of Patent: May 27, 2008

(54) STENT-GRAFT ASSEMBLY WITH ELUTION OPENINGS

(75) Inventor: Mark Dolan, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 616 days.

(21) Appl. No.: 10/420,553

(22) Filed: Apr. 22, 2003

(65) Prior Publication Data

US 2004/0215213 A1 Oct. 28, 2004

(51) Int. Cl.
*A61F 2/06* (2006.01)
(52) U.S. Cl. .................... 623/1.13; 623/1.14
(58) Field of Classification Search ........... 623/1.11–3, 623/1.17, 1.36, 1.13, 1.42, 1.44, 1.23, 1.14
See application file for complete search history.

(56) References Cited

U.S. PATENT DOCUMENTS

| | | | |
|---|---|---|---|
| 4,739,762 A | 4/1988 | Palmaz | |
| 5,133,732 A | 7/1992 | Wiktor | |
| 5,292,331 A | 3/1994 | Boneau | |
| 5,421,955 A | 6/1995 | Lau et al. | |
| 5,522,881 A * | 6/1996 | Lentz | 623/1.13 |
| 5,591,195 A * | 1/1997 | Taheri et al. | 623/1.11 |
| 5,667,523 A * | 9/1997 | Bynon et al. | 623/1.13 |
| 6,010,529 A * | 1/2000 | Herweck et al. | 623/23.69 |
| 6,090,127 A | 7/2000 | Globerman | |
| 6,248,128 B1 * | 6/2001 | Berry et al. | 623/1.17 |
| 6,270,523 B1 * | 8/2001 | Herweck et al. | 623/1.13 |
| 6,296,661 B1 * | 10/2001 | Davila et al. | 623/1.13 |
| 6,451,047 B2 * | 9/2002 | McCrea et al. | 623/1.13 |
| 6,475,232 B1 * | 11/2002 | Babbs et al. | 623/1.13 |
| 6,558,414 B2 * | 5/2003 | Layne | 623/1.13 |
| 6,579,307 B2 * | 6/2003 | Sarac | 623/1.13 |
| 6,592,614 B2 * | 7/2003 | Lenker et al. | 623/1.13 |
| 6,613,084 B2 * | 9/2003 | Yang | 623/1.42 |
| 6,645,241 B1 * | 11/2003 | Strecker | 623/1.13 |
| 6,652,541 B1 * | 11/2003 | Vargas et al. | 606/153 |
| 6,699,277 B1 * | 3/2004 | Freidberg et al. | 623/1.13 |
| 6,723,116 B2 * | 4/2004 | Taheri | 623/1.11 |
| 6,808,533 B1 * | 10/2004 | Goodwin et al. | 623/1.13 |
| 6,849,088 B2 * | 2/2005 | Dehdashtian et al. | 623/1.36 |
| 6,852,122 B2 * | 2/2005 | Rush | 623/1.13 |
| 6,878,161 B2 * | 4/2005 | Lenker | 623/1.13 |
| 6,911,040 B2 * | 6/2005 | Johnson et al. | 623/1.13 |
| 6,929,658 B1 * | 8/2005 | Freidberg et al. | 623/1.13 |
| 6,936,066 B2 * | 8/2005 | Palmaz et al. | 623/1.13 |
| 7,018,401 B1 * | 3/2006 | Hyodoh et al. | 623/1.12 |
| 2001/0000188 A1 * | 4/2001 | Lenker et al. | 623/1.13 |

(Continued)

OTHER PUBLICATIONS

Babbs, WO 98/25544, Published Jun. 18, 1998; Int'l App. # PCT/US97/22586, Filed Dec. 10, 1997.*

*Primary Examiner*—Todd E. Manahan
*Assistant Examiner*—Michael G Mendoza

(57) ABSTRACT

The present invention provides a stent-graft assembly. The assembly comprises at least one stent framework and a graft member. The graft member is positioned adjacent an inner surface of the stent framework and everted over an outer surface of the stent framework to enclose at least a portion of the stent framework. The assembly may further comprise a therapeutic agent that is enclosed by the graft member. Elution openings may be formed in the graft member to preferentially elute a therapeutic agent into the wall rather than the lumen of a vessel into which the stent-graft assembly is placed.

6 Claims, 5 Drawing Sheets

U.S. PATENT DOCUMENTS

2003/0130718 A1* 7/2003 Palmas et al. ............. 623/1.12
2003/0171801 A1* 9/2003 Bates ....................... 623/1.13
2003/0229389 A1* 12/2003 Escano ..................... 623/1.13

* cited by examiner

STENT-GRAFT ASSEMBLY WITH ELUTION OPENINGS

TECHNICAL FIELD

This invention relates generally to biomedical devices that are used for treating vascular conditions. More specifically, the invention relates to a stent-graft assembly that includes elution openings to deliver a therapeutic agent preferentially to a vessel wall rather than to a vessel lumen.

BACKGROUND OF THE INVENTION

Stents are generally cylindrical-shaped devices that are radially expandable to hold open a segment of a vessel or other anatomical lumen after implantation into the body lumen.

Various types of stents are in use, including expandable and self-expanding stents. Expandable stents generally are conveyed to the area to be treated on balloon catheters or other expandable devices. For insertion, the stent is positioned in a compressed configuration along the delivery device, for example crimped onto a balloon that is folded or otherwise wrapped about a guide wire that is part of the delivery device. After the stent is positioned across the lesion, it is expanded by the delivery device, causing the diameter to expand. For a self-expanding stent, commonly a sheath is retracted, allowing expansion of the stent.

Stents are used in conjunction with balloon catheters in a variety of medical therapeutic applications, including intravascular angioplasty. For example, a balloon catheter device is inflated during percutaneous transluminal coronary angioplasty (PTCA) to dilate a stenotic blood vessel. The stenosis may be the result of a lesion such as a plaque or thrombus. When inflated, the pressurized balloon exerts a compressive force on the lesion, thereby increasing the inner diameter of the affected vessel. The increased interior vessel diameter facilitates improved blood flow. Soon after the procedure, however, a significant proportion of treated vessels restenose.

To prevent restenosis, stents, constructed of a metal or polymer, are implanted within the vessel to maintain lumen size. The stent acts as a scaffold to support the lumen in an open position. Configurations of stents include a cylindrical sleeve defined by a mesh, interconnected stents, or like segments. Exemplary stents are disclosed in U.S. Pat. No. 5,292,331 to Boneau, U.S. Pat. No. 6,090,127 to Globerman, U.S. Pat. No. 5,133,732 to Wiktor, U.S. Pat. No. 4,739,762 to Palmaz and U.S. Pat. No. 5,421,955 to Lau.

Stent insertion may cause undesirable reactions such as inflammation, infection, thrombosis, and proliferation of cell growth that occludes the passageway. Stents have been used with coatings to deliver drugs or other therapeutic agents at the site of the stent that may assist in preventing these conditions. In some methods of producing a stent designed to deliver a drug, the drug coating is applied to a stent framework. This may result in the drug being delivered to only those portions of the vessel in direct contact with the stent, providing as little as 20% coverage.

When a graft is used in conjunction with a stent, 100% coverage of the portion of the vessel in direct contact with the graft is possible. The graft component of a stent-graft may also aid in minimizing thrombosis, preventing embolic events, and minimizing contact between the fissured plaque and the hematological elements in the bloodstream.

In addition, the graft component makes the device suitable for use in treating aneurysms. An aneurysm is a bulge or sac that forms in the wall of a blood vessel. The force of normal blood pressure in the aneurysm may cause the vessel to rupture. Aneurysms are most commonly the result of fatty deposits on the vessel wall but may also result from other causes that weaken the vessel wall, including heredity, trauma, or disease.

A number of methods and devices have been developed for treating aneurysms. A standard treatment is surgery, which is performed to replace the section of the vessel where the aneurysm has formed. Some patients are not good candidates for such open surgery, and, due to the highly invasive nature of the open procedure, other patients may not wish to undergo the treatment.

An alternative treatment is a technique known as endovascular stent grafting. In this procedure, a stent-graft is placed inside the vessel affected by the aneurysm in order to reinforce the weakened vessel wall, thereby preventing rupture of the aneurysm. Like stents, stent-grafts are delivered to the area to be treated using balloon catheters or other expandable devices. Certain therapeutic agents may be effective against the formation or progression of aneurysms. Therefore, it may be desirable to use a stent-graft to deliver these therapeutic agents to the site of an aneurysm.

Various methods have been devised to produce stent-grafts. Some of these, such as methods that involve stitching the graft material to the stent, can be labor intensive or may provide inadequate adherence of the graft material to the stent. Other methods may produce devices that cannot deliver the therapeutic agents efficiently. Therefore, it would be desirable to have a stent-graft assembly that overcomes the aforementioned and other disadvantages.

SUMMARY OF THE INVENTION

One aspect of the present invention is a stent-graft assembly comprising at least one stent framework and a graft member. The graft member is positioned adjacent an inner surface of the stent framework and everted over an outer surface of the stent framework to enclose at least a portion of the stent framework.

Another aspect of the present invention is a stent-graft assembly comprising at least one stent framework, a therapeutic agent, and a graft member. The graft member encloses the therapeutic agent and at least a portion of the stent framework.

Yet another aspect of the present invention is a system for treating a vascular condition, comprising a catheter and a stent-graft assembly operably coupled to the catheter. The stent-graft assembly includes at least one stent framework and a graft member. The graft member is positioned adjacent an inner surface of the stent framework and everted over an outer surface of the stent framework to enclose at least a portion of the stent framework.

A further aspect of the present invention is a method of manufacturing a stent-graft assembly. A graft member is positioned within a stent framework. First and second end portions of the graft member are everted over an outer surface of the stent framework. The first end portion is attached to the second end portion.

The aforementioned and other features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims and equivalents thereof.

DETAILED DESCRIPTION OF THE PRESENTLY PREFERRED EMBODIMENTS

Figure 1:
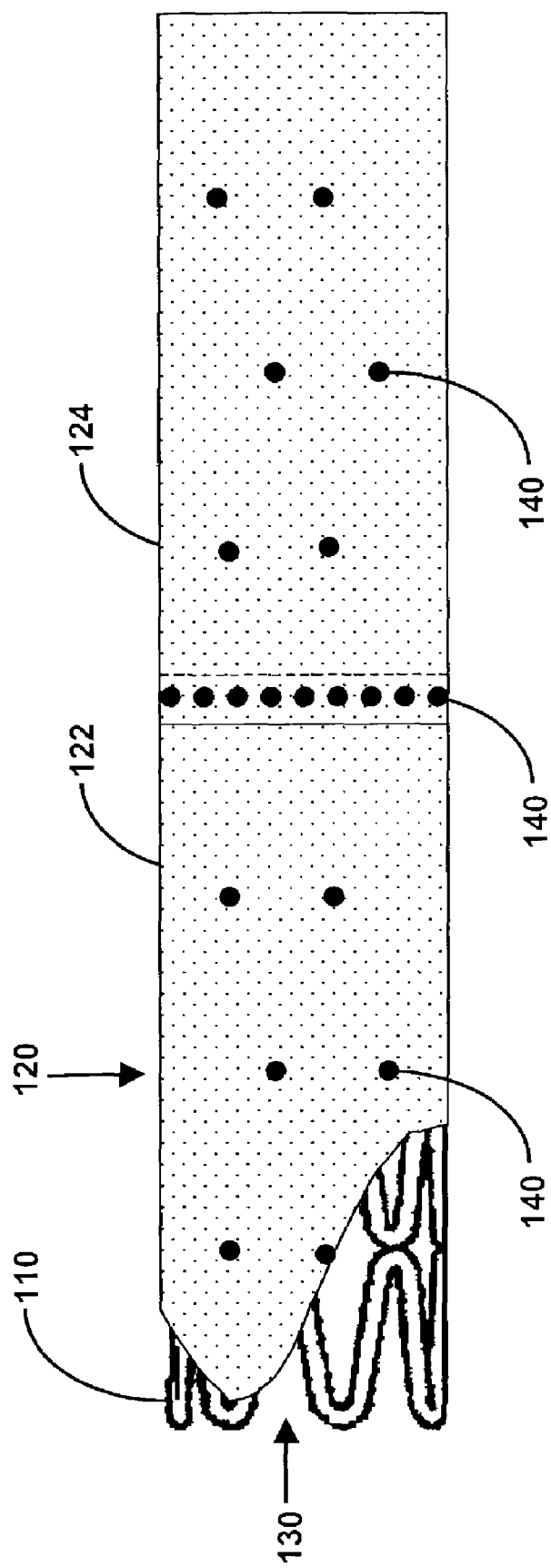
FIG. 1 is an illustration of one embodiment of a stent-graft assembly in accordance with the present invention.

One aspect of the present invention is a stent-graft assembly. One embodiment of the assembly, in accordance with the present invention, is illustrated in FIG. 1. The assembly comprises a stent framework 110, a graft member 120, and a therapeutic agent 130. Graft member 120 is shown partially cut away to reveal stent framework 110. Graft member 120 includes a first end portion 122 and a second end portion 124.

Stent framework 110 may be made from a wide variety of medical implantable materials such as stainless steel, nitinol, tantalum, ceramic, nickel, titanium, aluminum, polymeric materials, MP35N, stainless steel, titanium ASTM F63-83 Grade 1, niobium, high carat gold K 19-22, combinations of the above, and the like. The assembly may include one stent framework, as shown, or multiple stent frameworks.

Graft member 120 is positioned adjacent an inner surface of the stent framework and everted over an outer surface of the stent framework to enclose at least a portion of the stent framework. Graft member 120 is formed from an expandable biocompatible material such as polytetrafluoroethylene (PTFE), expanded polytetrafluoroethylene (ePTFE), spun polyester, or Dacron. The graft member material may be either porous or nonporous. The graft member may be manufactured in the shape of a tube, or a flat sheet of graft member material may be formed into a tube-like shape prior to positioning the graft member within the stent framework.

Therapeutic agent 130 is disposed on either or both of the graft member and the stent framework and is enclosed by graft member 120. For example, therapeutic agent 130 may be coated onto an outer surface of both the graft member and the stent framework. When the graft member is everted over the stent framework, the therapeutic agent becomes enclosed within the envelope formed by the portion of the graft member inside the stent framework and the portion that is everted over the outer surface of the stent framework. Therapeutic agent 130 may be, for example, an antineoplastic agent, an antiproliferative agent, an antibiotic, an anti-inflammatory agent, combinations of the above, and the like.

Graft member 120 is shown in FIG. 1 with first end portion 122 and second end portion 124 everted over an outer surface of the stent framework and attached one to the other to enclose the entire stent framework. As shown, the end portions have been overlapped and bonded at attachment points 140 using, for example, adhesive rivets or ultrasonic bonding.

One skilled in the art will recognize that the graft member may be everted into a variety of configurations to enclose all or a portion of the stent framework. Examples of configurations other than that shown in FIG. 1 include, but are not limited to, the following. A first end portion may be everted over the outer surface of the stent framework and attached to the second end portion at any point along the length of the stent framework, just beyond the edge of the stent framework, through the stent framework, or by folding the first portion back within the stent framework and attaching the first portion to the second portion within the stent framework. Alternatively, one or both end portions may be everted over the stent framework and attached to a mid-portion of the graft member.

To ensure that the inner portion of the graft member (that portion adjacent the inner surface of the stent framework) does not billow and impede the flow of blood through the stent-graft assembly, the inner portion of graft member 130 is attached to the outer portion (that portion everted over the outer surface of the stent framework) through openings in the stent framework. As shown in FIG. 1, attachment points 140 are positioned at multiple locations across the stent-graft assembly.

Figure 2:
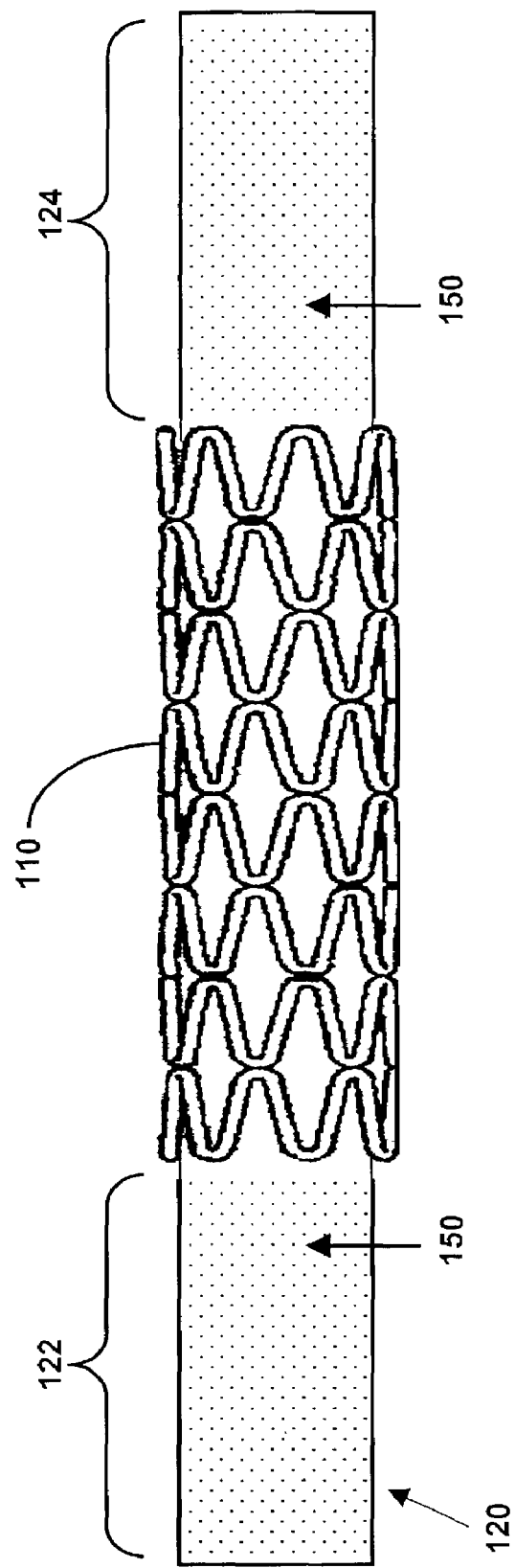
FIG. 2 is an illustration of the stent-graft assembly shown in FIG. 1, prior to everting the graft.

The stent-graft assembly may additionally include elution openings for eluting a therapeutic agent. The openings may be formed by, for example, puncturing holes into the graft member using a punch, a laser, or any other appropriate tool known in the art. Elution openings 150 are indicated in FIG. 2, where graft member 120 is shown prior to first end portion 122 and second end portion 124 being everted over the outer surface of stent framework 110. Once the end portions have been everted, the elution openings will be positioned over an outer surface of the stent framework, eluting the therapeutic agent preferentially into the vessel wall rather than into the vessel lumen. Rate of elution of the therapeutic agent may be controlled by the size and number of the therapeutic agent elution openings. Where the assembly does not contain therapeutic agent elution openings, the rate of elution may be controlled by the porosity of the graft member.

Figure 3:
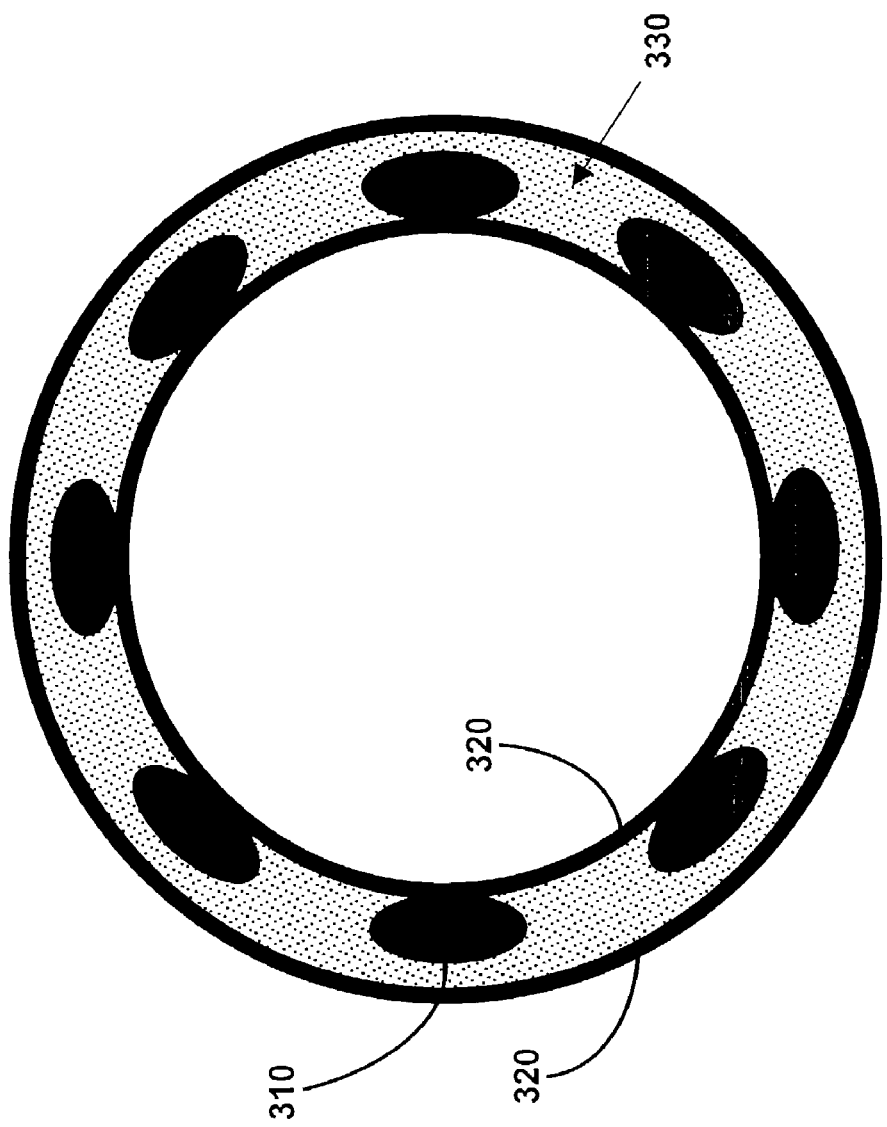
FIG. 3 is a cross-section of an embodiment of a stent-graft assembly including a therapeutic agent, in accordance with the present invention.

FIG. 3 shows a cross-section of a stent-graft assembly in accordance with the present invention that includes a therapeutic agent. The assembly comprises a stent framework 310, a graft member 320, and a therapeutic agent 330. Graft member 320 encloses therapeutic agent 330 and at least a portion of stent framework 310. The assembly may include elution openings, which may be formed in graft member 320 and positioned over an outer surface of stent framework 310.

A stent-graft assembly in accordance with the present invention may, of course, include neither a therapeutic agent nor therapeutic agent elution openings. Such an assembly may serve to reinforce a weakened or diseased vessel wall or act as a scaffold to support the vessel lumen in an open or expanded position without delivering a therapeutic agent.

Figure 4:
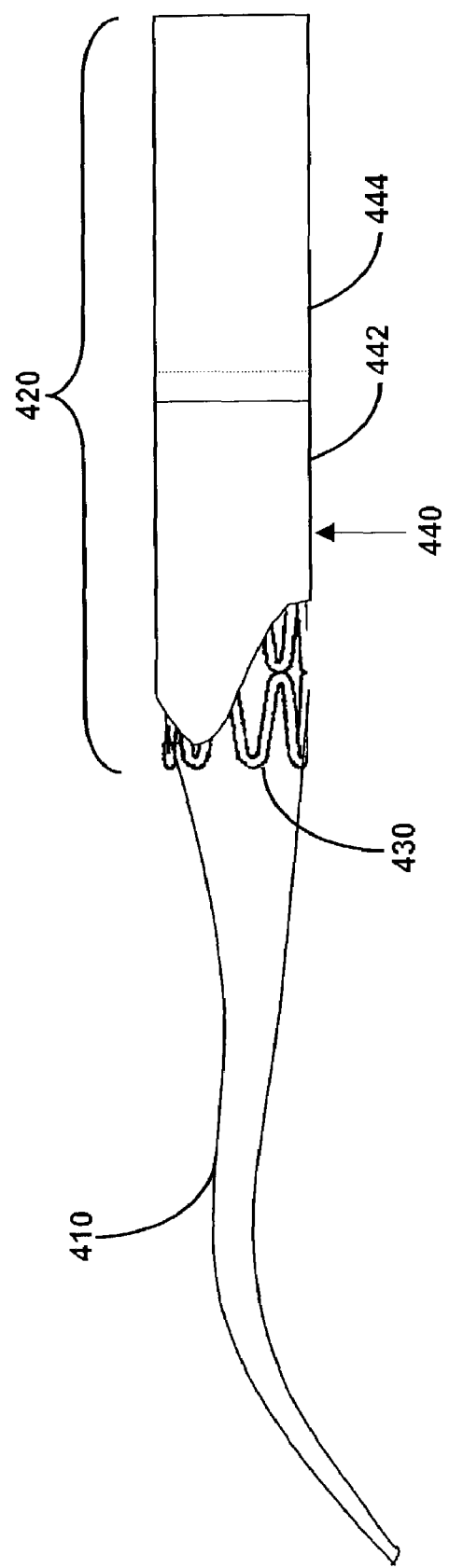
FIG. 4 is an illustration of one embodiment of a system for treating a vascular condition, in accordance with the present invention.

Another aspect of the present invention is a system for treating a vascular condition. One embodiment of the system, in accordance with the present invention, is illustrated in FIG. 4. The system comprises a catheter 410 and a stent-graft assembly 420 operably coupled to the catheter. Stent-graft assembly 420 includes a stent framework 430 and a graft member 440. Graft member 440 includes a first end portion 442 and a second end portion 444. Graft member 440 is shown partially cut away to reveal stent framework 430.

Catheter 410 may include a balloon to expand the stent, or it may include a sheath that retracts to allow expansion of a self-expanding stent. Both types of catheter are well known in the art. Stent-graft assembly 420 is shown coupled to catheter 410 for delivery within a vessel.

Stent framework 430 may be made from a wide variety of medical implantable materials such as stainless steel, nitinol, tantalum, ceramic, nickel, titanium, aluminum, polymeric materials, MP35N, stainless steel, titanium ASTM F63-83 Grade 1, niobium, high carat gold K 19-22, combinations of the above, and the like. The assembly may include one stent framework, as shown, or multiple stent frameworks.

Graft member 440 is formed from an expandable biocompatible material such as polytetrafluoroethylene (PTFE), expanded polytetrafluoroethylene (ePTFE), spun polyester, or Dacron. The graft member material may be either porous or nonporous.

Graft member 440 is shown positioned adjacent an inner surface of the stent framework, with first end portion 442 and second end portion 444 everted over an outer surface of the stent framework, overlapped, and attached one to the other to enclose the entire stent framework. One skilled in the art will recognize that the graft member may be everted in a variety of configurations other than that shown in FIG. 4 and may enclose the entire stent framework or a portion of the stent framework.

The system may include a therapeutic agent such as an antineoplastic agent, an antiproliferative agent, an antibiotic, an anti-inflammatory agent, combinations of the above, and the like. When included, the therapeutic agent is enclosed by graft member 440. The therapeutic agent may be eluted through pores in the graft member, with the rate of elution being controlled by the pore size. Graft member 440 may additionally include elution openings formed by, for example, mechanically puncturing holes into the graft member. The elution openings may be positioned over an outer surface of the stent framework, eluting a therapeutic agent preferentially into the vessel wall rather than into the vessel lumen. Rate of elution of the therapeutic agent may be controlled by the size and number of the openings.

Figure 5:
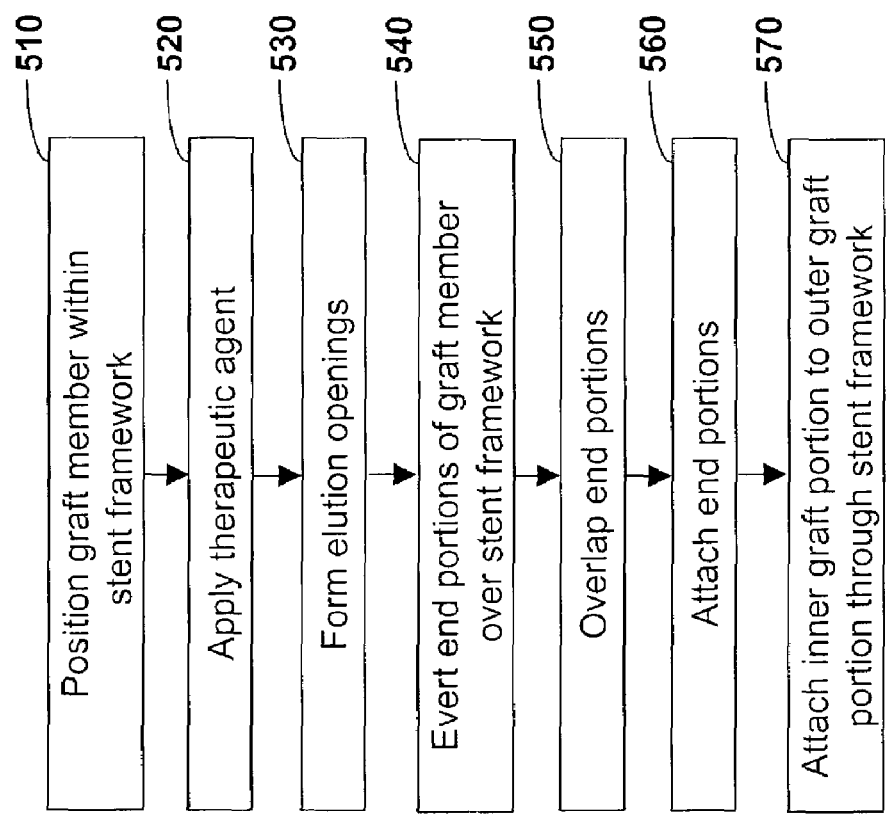
FIG. 5 is a flow diagram of one embodiment of a method of manufacturing a stent-graft assembly, in accordance with the present invention.

A further aspect of the present invention is a method of manufacturing a stent-graft assembly. FIG. 5 shows a flow diagram of one embodiment of a method in accordance with the present invention.

In this embodiment, a graft member, for example an ePTFE tube, is positioned within a stent framework (Block 510). This may be accomplished by, for example, inserting the graft member into the stent framework or by placing the graft member onto a mandrel and then placing the stent framework over the graft member.

A therapeutic agent is applied to at least a portion of either or both of the stent framework and the graft member (Block 520). Appropriate methods of applying the therapeutic agent include, but are not limited to, dipping, spraying, pad printing, inkjet printing, rolling, painting, micro-spraying, wiping, electrostatic deposition, vapor deposition, epitaxial growth, and combinations thereof. As just one example, the therapeutic agent may be contained in a gel that is sprayed onto the outer surface of the stent framework and the graft member.

Therapeutic agent elution openings are formed in the graft member (Block 530). The openings may be formed by, for example, puncturing holes into the graft member using a punch, a laser, or another appropriate tool.

In this embodiment, elution openings are formed in both the first and second end portions of the graft member, which are then everted over the outer surface of the stent framework (Block 540). The elution openings are thereby positioned over the outer surface of the stent framework, providing a means for the therapeutic agent to elute preferentially into the vessel wall rather than into the vessel lumen.

The graft member end portions are overlapped (Block 550) and attached one to the other (Block 560). The end portions may be attached by, for example, bonding the portions using adhesive rivets. An adhesive rivet may be formed by puncturing a hole through two or more layers of graft member material, forming a rivet end on the distal surface of the inner graft member layer, drawing the adhesive back through all graft member layers, and forming another rivet end on the proximal surface of the outer graft member layer. Other appropriate methods such as ultrasonic bonding may be used. The two end portions should be securely attached to ensure that the therapeutic agent is fully enclosed and will not leak out where the end portions are attached.

The inner graft portion (that portion adjacent the inner surface of the stent framework) is attached to the outer graft portion (that portion everted over the outer surface of the stent framework) through the stent framework at multiple attachment points (Block 570). Attaching the inner and outer portions of the graft member together ensures that the inner portion of the graft member remains positioned against the inner surface of the stent framework and does not billow and impede the flow of blood through the stent-graft assembly.

While the embodiments of the invention disclosed herein are presently considered to be preferred, various changes and modifications can be made without departing from the spirit and scope of the invention. The scope of the invention is indicated in the appended claims, and all changes and modifications that come within the meaning and range of equivalents are intended to be embraced therein.

What is claimed is:

1. A method of manufacturing a stent-graft assembly, comprising:
    positioning a graft member within a stent framework such that a first end proton and a second end portion of said graft extend past the stent frame work, the graft member comprising a non-porous material;
    puncturing only the first and second end portions of the graft member that extend past the stent framework to form elution openings in first and second end portions of the graft member based on a predetermined rate of elution such that the graft member within the stent framework remains non-porous;
    applying a therapeutic agent to at least a portion of one of the graft member and the stent framework prior to everting first and second end portions of the graft member over an outer surface of the stent framework;
    everting first and second end portions of the graft member over an outer surface of the stent framework; and
    attaching the first end portion to the second end portion.

2. The method of claim 1 wherein attaching the first end portion to the second end portion comprises overlapping the end portions and attaching them one to the other.

3. The method of claim 1 further comprising:
    attaching an inner portion of the graft member to an outer portion of the graft member through openings in the stent framework.

4. A stent-graft assembly manufactured according to the method of claim 1.

5. A stent-graft assembly manufactured according to the method of claim 2.

6. A stent-graft assembly manufactured according to the method of claim 3.

* * * * *